United States Patent
Chen et al.

(10) Patent No.: US 12,347,542 B2
(45) Date of Patent: Jul. 1, 2025

(54) PREDICTING EXERCISES BASED ON USER-SELECTED VARIANCE

(71) Applicant: FITBOD, INC., San Francisco, CA (US)

(72) Inventors: Allen Chen, San Francisco, CA (US); Jess Venticinque, Woodside, CA (US)

(73) Assignee: FITBOD, INC., San Francisco, CA (US)

( * ) Notice: Subject to any disclaimer, the term of this patent is extended or adjusted under 35 U.S.C. 154(b) by 467 days.

(21) Appl. No.: 17/233,238

(22) Filed: Apr. 16, 2021

(65) Prior Publication Data

US 2022/0336077 A1 Oct. 20, 2022

(51) Int. Cl.
*G16H 20/30* (2018.01)
*A63B 24/00* (2006.01)

(52) U.S. Cl.
CPC ......... *G16H 20/30* (2018.01); *A63B 24/0075* (2013.01)

(58) Field of Classification Search
CPC ............................ G16H 20/30; A63B 24/0075
See application file for complete search history.

(56) References Cited

U.S. PATENT DOCUMENTS

| | | | |
|---|---|---|---|
| 11,621,067 B1 | 4/2023 | Nolan | |
| 2011/0281249 A1* | 11/2011 | Gammell | G16H 10/20 434/247 |
| 2014/0080108 A1 | 3/2014 | Zimmerman | |
| 2016/0144236 A1 | 5/2016 | Ko et al. | |
| 2018/0001181 A1 | 1/2018 | Von Prellwitz et al. | |
| 2018/0071583 A1 | 3/2018 | Paiz et al. | |
| 2018/0133551 A1 | 5/2018 | Chang et al. | |
| 2020/0211410 A1 | 7/2020 | Kang | |
| 2021/0008413 A1 | 1/2021 | Asikainen et al. | |
| 2021/0056643 A1* | 2/2021 | Narula | G06F 16/9535 |
| 2021/0121740 A1 | 4/2021 | Lynch | |

(Continued)

FOREIGN PATENT DOCUMENTS

WO  WO-2008030484 A2 *  3/2008  .......... A61B 5/0022

OTHER PUBLICATIONS

Meishan Ai, et al. "Resting-State MRI Functional Connectivity as a Neural Correlate of Multidomain Lifestyle adherence in older adults at risk of Alzheimer's disease" 2023, Scienific Reports. (Year: 2023).*

(Continued)

*Primary Examiner* — Raquel Alvarez
(74) *Attorney, Agent, or Firm* — Fenwick & West LLP (57) ABSTRACT

An exercise recommendation system determines workout plans for users. The exercise recommendation system receives a profile of a user and a level of variance selected by the user. The profile includes a history of exercises the user has performed, available gym equipment, and exercise goals. The exercise recommendation system inputs the profile to a machine learning model configured to rank a set of exercises for a user to perform. The exercise recommendation system modifies the ranking of exercises based on the level of variance selected by the user. Modification of the ranking is greater for a first level of variance than for a second level of variance less than the first level of variance. The exercise recommendation system generates a workout plan for display within a user interface to the user based on the modified ranking.

20 Claims, 5 Drawing Sheets

(56) References Cited

U.S. PATENT DOCUMENTS

| | | |
|---|---|---|
| 2021/0162261 A1 | 6/2021 | Neumann |
| 2021/0241137 A1 | 8/2021 | Jain et al. |
| 2022/0016483 A1 | 1/2022 | Wiebe et al. |
| 2022/0023718 A1 | 1/2022 | Augustin et al. |
| 2022/0226695 A1 | 7/2022 | Madonna et al. |
| 2022/0314073 A1 | 10/2022 | Bissonnette et al. |

OTHER PUBLICATIONS

Juneau, C. "Build Muscle Faster With A Smart Program That Levels Up Automatically With You," Dr. 2024 Muscle, Retrieved from the internet <URL:https://drmuscleapp.com/48.html>.

Tran, T. T. et al. "Recommender System with Artificial Intelligence for Fitness Assistance System," 15th International Conference on Ubiquitous Robots, Jun. 26-30, 2018, 4 pages.

United States Office Action, U.S. Appl. No. 17/233,246, filed Jun. 27, 2023, 14 pages.

Venticinque, J. "Building Data-Driven Fitness with Fitbod," Jun. 3, 2016, 8 pages.

youtube.com, "Fitbod—The Best Fitness & Gym App Review," uploaded by Josh Marriott—Real Estate Training, Dec. 2, 2018, 1 page, Retrieved from the internet <URL:https://www.youtube.com/watch?v=Z45zl8FFhgA>.

youtube.com, "Fitbod Review | A Dive Into the Best Fitness App Yet," uploaded by TechnoFlux, Mar. 2, 2019, 1 page, Retrieved from the internet <URL:https://www.youtube.com/watch?v=NgSd8sdv0Sg>.

youtube.com, "Fitbod Demo," uploaded by allenchen4783, Nov. 13, 2015, 1 page, Retrieved from the internet <URL:https://www.youtube.com/shorts/0m9g8202ubA>.

youtube.com, "E730: Launch Incubator PT1: Transported: Real Estate VR & FitBod: Machine learning strength-training," uploaded by This Week in Startups, May 5, 2017, 1 page, Retrieved from the internet <URL:https://www.youtube.com/watch?v=2yjamisdBVg>.

youtube.com, "Fitbod Fitness App Review (An AI Personal Trainer, Sort of)," uploaded by Average Dad Reviews Fitness, Jan. 11, 2021, 1 page, Retrieved from the internet <URL:https://www.youtube.com/watch?v=xag1Y0E-NCU>.

\* cited by examiner

System Environment
100

PREDICTING EXERCISES BASED ON USER-SELECTED VARIANCE

BACKGROUND

This invention relates generally to determining a workout plan for a user and, more particularly, to using machine learning to determine exercises, weights, and capabilities for users.

When working out, users may follow different workout plans from one another. For example, one user may want to focus on arm exercises one day and leg exercises the next day with a goal to strengthen their muscles each day. In another example, a user may prefer that the exercises in their workout be the same every week, while another user may prefer to perform a greater variety of exercises when working out. However, current systems do not allow a user to specify that they would like variety in their workout while accounting for the user's goals and other preferences in determining a workout for the user.

Further, some users may want to increase their capabilities when they work out, such as by increasing a weight that they use or number of repetitions they perform of an exercise over time. However, current systems lack the ability to predict a user's capability based on their previous exercises and how recently they worked out. Thus, a system that determines a user's capability for exercises is necessary.

SUMMARY

The following disclosure describes an exercise recommendation system that selects exercises for a user to perform. In particular, the exercise recommendation system receives a profile of a user and a level of variance selected by the user. The profile may include a history of exercises the user has performed, available gym equipment, and one or more exercise goals. The exercise recommendation system inputs the profile of the user to an exercise selection model, which is configured to rank a set of exercises for a user to perform based on the history of exercises the user has performed, the available gym equipment, and the one or more exercise goals. The exercise recommendation system modifies the ranking of exercises based on the level of variance selected by the user. Modification of the ranking of exercises is greater for a first level of variance than for a second level of variance less than the first level of variance. The exercise recommendation system generates a workout plan for display within an interface to a user based on the modified ranking.

In some embodiments, the exercise recommendation system also selects target weights for users. In particular, the exercise recommendation system accesses a plurality of exercise pairs. Each exercise pair is associated with a weight and labeled with performance statistics of users who have completed the exercises of the exercise pair. The exercise recommendation system trains a machine learning model using the plurality of exercise pairs. The machine learning model is configured to determine a weight to recommend to a user for a first exercise based on performance statistics of user associated with one or more second exercises, where each second exercise is within an exercise pair with the first exercise. The exercise recommendation system retrieves performance statistics of a target user including a weight for each of one or more exercises previously performed by the target user. The exercise recommendation system applies the machine learning model to the retrieved performance statistics to determine, for a target exercise, a target weight to recommend to the target user for the target exercise. The exercise recommendation system modifies an interface displayed by a client device of the target user to include the target weight.

In further embodiments, the exercise recommendation system determines current capabilities of users. In particular, the exercise recommendation system accesses an exercise history for a user. The exercise history comprises an exercise performed by the user and a capability of the user each time the user performed the exercise. The exercise recommendation system partitions the exercise history into a plurality of time periods. For each time period, the exercise recommendation system computes an aggregate capability of the user for the exercise based on the capabilities of the user in performing the exercise during the time period. The exercise recommendation system calculates a moving average capability of the user for the exercise based on the aggregate capabilities. The exercise recommendation system determines a current capability of the user for the exercise based on the moving average capability. The current capability of the user for the exercise is discounted at least in part based on how recently the user performed the exercise.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
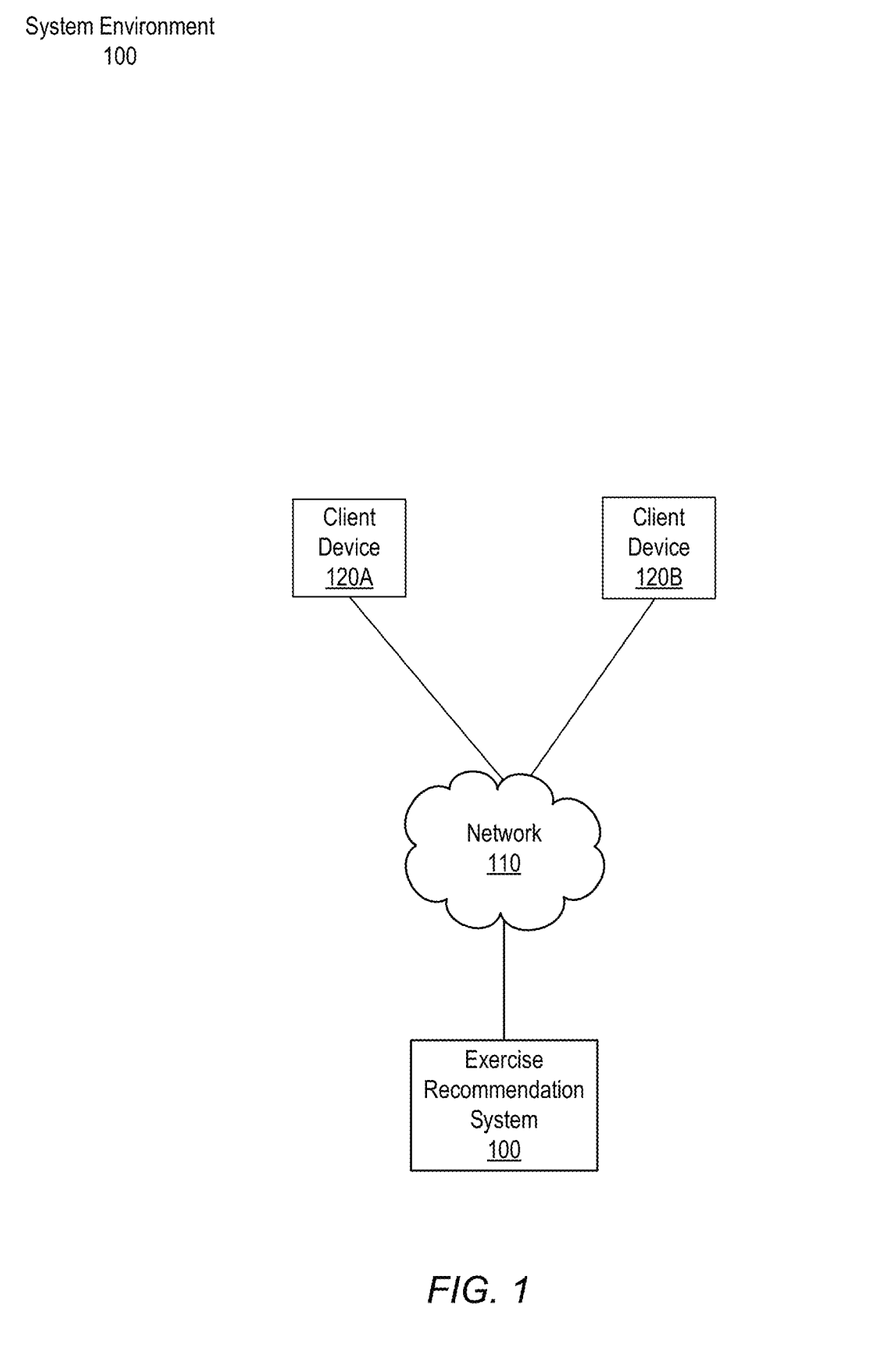
FIG. 1 illustrates a system environment for an exercise recommendation system, according to one embodiment.

FIG. 1 illustrates a system environment for an exercise recommendation system 100, according to one embodiment. The exercise recommendation system 100 is connected to a number of client devices 120 used by users of the exercise recommendation system 100 via a network 110. These various components are now described in additional detail.

The client devices 120 are computing devices such as smart phones, laptop computers, desktop computers, or any other device that can communicate with the exercise recommendation system 100 via the network 110. The client devices 120 may provide a number of applications, which may require user authentication before a user can use the applications, and the client devices 120 may interact with the exercise recommendation system 100 via an application. Though two client devices 120 are shown in FIG. 1, any number of client devices 120 may be connected to the cooking control system 100 in other embodiments.

Figure 2:
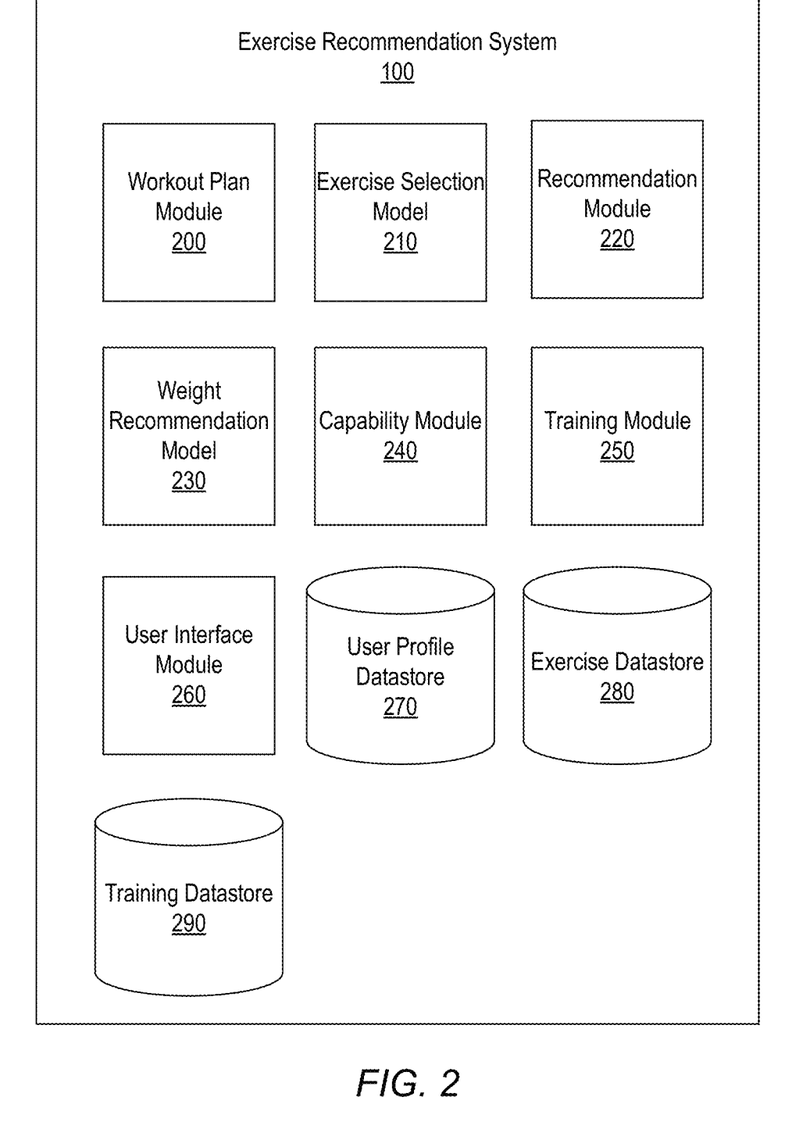
FIG. 2 is a high-level block diagram of an exercise recommendation system, according to one embodiment.

The network 110 connects the client devices 120 to the exercise recommendation system 100, which is further described in relation to FIG. 2. The network 110 may be any suitable communications network for data transmission. In an embodiment such as that illustrated in FIG. 1, the network 110 uses standard communications technologies and/or protocols and can include the Internet. In another embodiment, the network 110 use custom and/or dedicated data communications technologies.

FIG. 2 is a high-level block diagram of an exercise recommendation system 100, according to one embodiment. The exercise recommendation system 100 operates in real-time to determine exercises, target weights, target repetitions, capabilities, and the like for users. The exercise recommendation system 100 includes a workout plan module 200, an exercise selection model 210, a recommendation module 220, a weight recommendation model 230, a capability module 240, a training module 250, a user interface module 260, a user profile datastore 270, an exercise datastore 280, and a training datastore 290. In some embodiments, the exercise recommendation system 100 may include more modules or models than shown in FIG. 2 or one or more of the modules and models shown in FIG. 2 may be combined within the exercise recommendation system 100.

The workout plan module 200 determines workout plans for users. A workout plan includes one or more exercises for a user to complete during a workout (e.g., a continuous time period during which a user performs exercises). An exercise is an activity that a user performs to improve their physical fitness, and exercises are stored in the exercise datastore. Examples of exercises may include squats, leg lifts, jumping jacks, and the like. Each exercise is associated with exercise information, which may include an exercise type (e.g., cardio, bodyweight, weighted, warm-up, timed intervals, etc.), a list of users who have performed the exercise, and exercise requirements. Exercise requirements describe equipment needed to perform an exercise or physical ailments that may preclude a user from performing the exercise. Exercises and exercise information is stored in the exercise datastore 280.

The workout plan module 200 receives a request for a workout plan from the user interface module 260. The request can include a level of variance selected by the user via a user interface, as described in relation to the user interface module 260 below. The level of variance represents how much variety in exercise type, exercise, workout length, and focused muscle group the user would like in a workout. For instance, a high level of variance (e.g., 80%) indicates that a user prefers to perform a variety of exercises each workout whereas a low level of variance (e.g., 25%) indicates that a user prefer to perform the same exercises each workout. In some embodiments, the workout plan module 200 may use a default level of variance as the selected level of variance if the user has not explicitly selected a level of variance via the request. In other embodiments, the workout plan module 200 may specify a level of variance of the user based on a history of exercises performed by the user stored in the user profile datastore 270, as described below. For example, if the user has performed a certain number of workouts or number of exercises, the workout plan module 200 may automatically adjust level of variance to correspond to the user's history.

The workout plan module 200 retrieves a profile of the user from the user profile datastore 270. The user profile datastore 270 stores profiles of users, where each profile includes a current height, weight (which may be stored in pounds or kilograms), age, muscle mass, and level of fitness experience (e.g. beginner, intermediate, advanced, etc.) of a user. The profile may also include historical weights of the user, historical muscle masses of the user, gym equipment available to the user, one or more exercise goals selected by the user (e.g., number of calories to burn, desired weight, desired muscle mass, desired strength per exercise, desired type, format, or style of workout, etc.), ratings of exercises previously performed by the user, one or more muscle groups the user would like to target during workouts, and any exercise restrictions indicated by the user (e.g., the user has knee issues and cannot squat), and an exercise history of exercises previously performed by the user during one or more workouts. Each exercise in the exercise history may be associated with performance statistics of the user when the user completed the exercise and a recency (e.g., how recently the exercise was performed by the user). For instance, the performance statistics may include a weight the user used for the exercise (stored as pounds or kilograms), a number of sets the user completed of the exercise, a number of repetitions per set the user completed for the exercise, and a time to complete the exercise. The performance statistics may also include the user's current weight and muscle mass. Further, the exercise history may be associated with an exercise list for the user which includes exercises that match the user's profile (e.g., exercises that the user has equipment and ability to perform). The exercise list may alternatively be stored in the exercise datastore 280.

Each profile may also include a capability of a user. The capability is a maximum amount of weight that the user can use to do one repetition of an exercise. For example, the user's capability may be 150 pounds of weight doing one bench-press. In some embodiments, capability may include weight capability and repetition capability for a particular exercise (e.g., bench-press). A repetition capability may be a maximum number of repetitions the user can do of the exercise in a single set. For example, the user's weight capability may be using 150 pounds of weight to do one bench-press, and the user's repetition capability may be doing 20 bench-presses with 50 pounds of weight. In some embodiments, the repetition capability may be only used for bodyweight exercises that do not require the user o use extra weight. or a number of a weighted exercise in a set using a base weight. The capability (e.g., weight capability and repetition capability) of the user for an exercise may be stored in the exercise datastore 280 in association with the exercise in the user's exercise list. The capability module 240 may update the capability of the user for each exercise as the user completes exercises, as further described below.

The workout plan module 200 inputs the profile of the user to the exercise selection model 210. The exercise selection model 210 is a machine learning model configured to rank a set of exercises for a user to perform based on a profile of a user, including the exercise history that the user has performed (e.g., as stored in for the user's profile), gym equipment available to the user, and one or more exercise goals. The exercise selection model 210 may also be configured to rank the exercises based on exercise metadata stored in the exercise datastore 280. The exercise metadata may include a score for each exercise indicating an efficacy of the exercise and/or whether the exercise targets primary muscle groups (e.g., quadriceps, shoulders, back, etc.) or accessory muscle groups (e.g., abductors, forearms, calves, etc.). The exercise selection model 210 may be a classifier, decision tree, regression model, neural network, random forest model, or the like. In some embodiments, the exercise selection model 210 may be a statistical model. The exercise selection model 210 is trained by the training module 250, as described below.

The workout plan module 200 receives, from the exercise selection model 210, scores of exercises of the exercise datastore 280, which form a ranking of the exercises based on the scores. In some embodiments, the workout plan module 200 may store an exercise list specific to each user in the exercise datastore 280 such that the exercise selection model 210 may score and rank the exercises from the user's exercise list. In these embodiments, the exercise list may include exercises that the user has equipment for or that align with the exercise goals set by the user. The workout plan module 200 adjusts the ranking based on the profile of the user who submitted the request. For example, if the user's profile indicates that the user has a goal to improve their quad strength, the workout plan module 200 may boost scores for exercises that focus on strengthening quads by 1.5 times (or another multiplicative factor). In another example, if the user's profile indicates that they do not own dumbbells, the workout plan module 200 may reduce the scores of exercises that require dumbbells to zero or remove the exercises from the ranking.

The workout plan module 200 may also adjust the scores in the ranking based on the selected level of variance. In some embodiments, the workout plan module 200 may alter the ranking of exercises completed by the user within a threshold amount of time by the selected level of variance. For example, for a selected level of variance of 50%, the workout plan module 200 may randomly select 50% of the exercises the user most recently performed (e.g., within a threshold amount of item) and increase their rankings by 5 places. The workout plan module 200 may additionally decrease the rankings of the other 50% of exercises most recently performed by 5 places. The workout plan module 200 may reduce the scores of exercises recently performed by the user, exercises with low ratings by the user (e.g., on a scale from 1 to 5, a 3 or less), or exercises that require equipment the user does not have by a set amount (e.g., subtracting one from each score) or to zero. Alternatively, the workout plan module 200 may reduce the scores of exercises that the user does not have equipment for to zero or may alter the score by the level of variance (e.g., multiplying a subset of the scores by the level of variance).

The workout plan module 200 selects one or more of the exercises for the user's workout plan based on the ranking. For instance, the workout plan module 200 may select the top ten ranked (or another threshold number of) exercises from the exercise list send those to the user interface module 260 for display to the user as the user's workout plan. In some embodiments, the workout plan module 200 may select the top-ranked exercise to send to the user interface module 260 for display to the user and may use the exercise selection model 210 to re-score and re-rank the exercises from the exercise list to select an next exercise for the user to perform upon receiving an indication from the user interface module 260. The workout plan module 200 may repeat this process until the workout plan module 200 has selected a threshold number of exercises for the user to perform. In other embodiments, the workout plan module 200 may select the top-ranked exercise and subsequently use the exercise selection model 210 to re-score and re-rank the exercises from the exercise list to select a next exercise. The workout plan module 200 may repeat this process of re-scoring, re-ranking, and selecting until the workout plan module 200 has selected a threshold number of exercises for the workout plan, which the workout plan module 200 sends to the user interface module 260 to display to the user as the workout plan.

Further, in some embodiments, the workout plan module 200 selects a subset of exercises to send for the workout plan based on the level of variance. For instance, the workout plan module 200 may select more exercises for a high level of variance than for a low level of variance. In these embodiments, the workout plan module 200 may randomly select exercises from the subset to send to the user interface module 260 for the workout plan upon receiving a request from the user interface module 260. Thus, the user may see a greater variety of exercises for a higher level of variance than a lower level of variance.

For each selected exercise, the workout plan module 200 request a recommended weight, number of repetitions, and number of sets (henceforth referred to collectively as recommendations) from the recommendation module 220. For example, the exercise "bicep curls" may be associated with a weight of 15 pounds per arm, 10 curls, and 3 sets for in the user's workout plan. To complete the exercise, the user could to use 15-pound dumbbells to do 10 bicep curls on each arm 3 times. The recommendation module 220 may determine a weight, number of repetitions, and number of sets to recommend to the user based on the user's performance statistics.

The recommendation module 220 may receive a request for the one or more of the recommendations for a user and an exercise from the workout plan module 200. Alternatively, the recommendation module 200 may receive a request for the one or more recommendations and the exercise from the user interface module 260. The recommendation module 220 retrieves performance statistics of the user who submitted the request from the user profile datastore 270 and uses the performance statistics to determine recommendations for the user. In some embodiments, if the user has previous performed the exercise, the recommendation module 220 may base the recommendations on the most recent performance statistics related to the exercise in the exercise in the history. In other embodiments, if the user has not performed the exercise, the recommendation module 220 may apply a ratio based on an exercise pair including the exercise and an exercise the user has performed to determine recommendations. Alternatively, the recommendation module 220 request a capability of the user from the capability module 240, which is described below, and use the capability of the user to determine recommendations for the user.

Further, the recommendation module 220 may input the performance statistics of the user to the weight recommendation model 230 to determine the recommendations. The weight recommendation model 230 is a machine learning model configured to determine a weight to recommend to a use for an exercise based on performance statistics of the user associated with other exercises. The weight recommendation model 230 may additionally receive the exercise as an input or may output a weight for each exercise in the exercise datastore 280. In some embodiments, the weight recommendation model 230 may also determine the number of repetitions and number of sets of the exercise to recommend to the user. The weight recommendation model 230 may be a classifier, decision tree, regression model, neural network, random forest model, or the like. The weight recommendation model 210 is trained by the training module 250, as described below.

In some embodiments, the recommendation model 220 receives recommendations directly from the weight recommendation model 230. In some embodiments, the recommendation module 220 may receive a score for each weight in a list of weights. For example, the list of weights may include weights from zero pounds to 200 pounds (or another upper limit of weight) at five-pound increments. The recommendation module 220 may access the user's profile and reduce the scores of weights that the user does not own to zero. The recommendation module may also reduce the scores of weights that do not align with the user's exercise goals or restrictions. For example, if the user's goal is "aerobic exercise," the recommendation module 220 may reduce the scores of weights that are over a third of the user's personal weight. The recommendation module 220 ranks the weights based on the scores and selects the highest-ranked weight to recommend to the user. The recommendation module 220 may similarly receive scores for one or more number of repetitions and/or number of sets from the weight recommendation model 230 and, after reducing one or more scores based on the user's profile, rank and select a number of repetitions and/or number of sets based on the ranking. The recommendation module 220 may send the recommendations to the user interface module 260 for display to a user or may send the selections to the workout plan module 200.

The workout plan module 200 receives the recommendations from the recommendation module 220 for each selected weight. The workout plan module 200 may determine an order for the exercises based on the ranking of exercises or may shuffle the exercises into an order randomly. The workout plan module 200 stores the order of exercises each associated with the received recommendations as a workout plan for the user in the exercise datastore 280. The workout plan may be stored in association with a current time/date and current performance statistics of the user in the exercise datastore 280. The workout plan module 200 send the workout plan to the user interface module 260 for display to the user. In some embodiments, the workout plan module 200 may receive indications from the user interface module 260 for each of the exercises in the workout plan indicating if the user completed the exercise using the recommendations or if the user modified the recommendations (e.g., performed another exercise, used a different weight, requested a different exercise, etc.). The workout plan module 200 stores a record of the indications in the exercise datastore 280 as part of the exercise history for the user.

In some embodiments, the user's exercise goals may indicate that they would like to perform exercises at their capability or the user may request their capability for an exercise via the user interface module 260. In these embodiments, the capability module 240 may receive the request from the user interface module 260 or may receive an indication from the user interface module 260 that the user inputted an exercise goal of performing at their capability. The capability module 240 may determine a current capability of the user in performing one or more exercises in response to receiving the request or indication.

In some embodiments, if the user has not performed the exercise, the capability module 240 may input the user's profile to a random forest model to determine the current capability of the user based on other user's capabilities. In other embodiments, the capability module 240 may use the capability of the user in performing other exercises to determine the user's current capability. For example, if the user has recently performed a bench-press and wants to know their current capability for a lateral press, the capability module 240 access a ratio for the two exercises (e.g., the bench-press and lateral press) stored in the exercise datastore 280. The capability module 240 applies the ratio to the capability of the user in performing the bench-press to determine the capability of the user in performing the lateral press. In further embodiments, the capability module 240 may calculate a moving average capability based on the user's exercise history if the user has performed the exercise before.

In particular, the capability module 240 accesses the exercise history of the user from the user profile datastore 270 to retrieve exercises performed by the user and a capability of the user each time the user performed the exercise. For example, the capability module 240 may retrieve exercise information indicating that the user has performed one bench-press using 150 pounds one week ago and one bench-press using 155 pounds one day ago. In some embodiments, the capability module 20 may only access the exercise history for one exercise specified by the request from the user and determine the user's capability for that exercise. Further, the capability module 240 may only access exercises of the exercise history performed within a recent time period (e.g., the last 180 days).

The capability module 240 partitions the exercise history into time periods. For instance, the capability module 240 may group exercises in the exercise history into one week time periods, one month time periods, or any other grouping of time. For each time period, the capability module 240 computes an aggregate capability of the user for each exercise based on the capability of the user when performing the exercise during the time period. The aggregate capability may be a sum, average, or another combination of the capability of the user for the exercise during the time period. For example, if the exercise history indicates that the user performed one bench-press using 150 pounds each day during the time period, the aggregate capability for the time period may be 150 pounds. Further, the capability module 240 may only average the capability for the exercise on days when the user actually performed the exercise and not include days where the user did not perform the exercise in computing the aggregate capability. The capability module 240 calculates a weighted moving average capability of the user based on the aggregate capabilities of the time period for each exercise. For instance, the capability module 240 may weight the aggregate capability of the most recent time period highest and the aggregate capability of the oldest time period the least.

The capability module 240 determines a current capability of the user for each exercise based on the moving average capability and a current time. In particular, the capability module 240 may use the moving average capability as the current capability or may apply exponential smoothing to the moving average capability to determine the current capability. However, if the current time is a threshold amount of time past the last time the user performed the exercise, the capability module 240 may discount the moving average capability based on how recently the user last performed the exercise. For instance, the capability module 240 may decay the moving average capability and may select a current capability from the decayed portion of the moving average capability if the user is performing the exercise more than a week (or another threshold time period) since the last performance of the exercise. The capability module 240 sends the selected current capability to the user interface module 250 for display and may store the current capability in the user's profile in the user profile datastore 270.

The training module 250 trains the exercise selection model 210 to rank a set of exercises of a user to perform based on the exercise history of the user, the gym equipment available to the user, and one or more exercise goals set by the user. In particular, the training module 250 may access the user profile datastore 270 to retrieve profiles of users. The training module 250 labels the exercise history of each user with the user's available exercise equipment, one or more exercise goals, and other aspects from the user's profile. The training module 250 stores the labeled exercise histories in the training datastore 290 as training data for the exercise selection model 210. In some embodiments, the training data may include training data for the exercise selection model 210 that was manually labeled by an external operator rather than the training module 250.

The training module 250 trains the exercise selection model 210 on the training data such that the exercise selection model 210 is configured to rank the set of exercises in the exercise datastore 280 upon receiving input of the user's profile, including the exercise history, available gym equipment, and exercise goals. In some embodiments, the exercise selection model 210 may comprise multiple machine learning models each trained for a particular user. In these embodiments, the training module 250 may train each machine learning model on training data specific to a user, and the workout plan module 200 may apply the machine learning model for the user. The training module 250 may train the exercise selection model 210 periodically as new users input profiles to the exercise recommendation system 100.

The training module 250 also trains the weight recommendation model 230 to determine a weight to recommend to a user for an exercise. The training module 250 accesses the exercise datastore 280 to retrieve a plurality of exercise pairs, which each includes two exercises. The training module 250 accesses the user profile datastore 270 to retrieve exercise histories of users and labels each exercise pair with performance statistics of users who completed both exercises of the pair. The performance statistics of the user include any weights used for exercises, number of repetitions of the exercises done by the user, and number of sets of the exercises done by the user, and, in some embodiments, each exercise in an exercise pair is associated with a particular weight and the exercise pair is labeled with the performance statistics of users who used the associated weight when performing the exercise. The training module 250 stores the labeled exercise pairs in the training datastore 290 as training data for the weight recommendation model 230.

The training module 250 trains the weight recommendation model 230 on the training data such that the weight recommendation model 230 is configured recommend a weight to a user for an exercise upon receiving performance statistics and the exercise. In some embodiments, weight recommendation model 230 may be further configured to determine a number of repetitions, number of sets, rest time between sets, interval time for each set, distance for an exercise (e.g., a mile, 100 meters, etc.), elevation, resistance, and/or resistance band tension to recommend to the user for the exercise. The training module 250 may train the weight recommendation model 230 periodically as more users complete exercises using the exercise recommendation system 100.

The user interface module 260 generates and transmits a user interface (or "interface") to one or more client devices 120 of users of the exercise recommendation system 100. The user interface may display exercises of workout plans determined by the workout plan module 200, recommended weights (or number of sets or repetitions) determined by the recommendation module 220, and capabilities determined by the capability module 240. The user interface may display interactive elements that allow a user to request a workout plan, recommendations, or a current capability for an exercise or indicate that they have completed an exercise or request a new exercise in the workout plan (such as by swiping away a presented exercise). For example, a user may indicate, via a sliding interactive element of the user interface, a selected level of variance for a workout plan. The user may also enter information for their profile and whether they completed one or more exercises via the user interface. The user interface module 260 may update the profile of a user in the user profile datastore 270 when a user adds or changes their information for their profile, such as by adding new exercise goals, rating exercises, and the like.

The user interface module 260 may display exercises for a workout plan to a user via the user interface. For instance, a user may input, via the user interface, a request for a workout plan. The request may be associated with a level of variance selected by the user on a sliding interactive element, which allows a user to configure how much variation from other workout plans the user would like for the workout plan. The user interface module 260 sends the request to the workout plan module 200, which determines a workout plan 200 to send back to the user interface module 260 for display to the user. In some embodiments, the user interface module 260 may send one exercise (and a weight, number of repetitions, and number of sets) at a time from the workout plan for display on the user interface, and upon receiving confirmation from the user via the user interface that the user performed the exercise, the user interface module 260 may update the user's exercise history in the user profile datastore 270. Further, the user interface module 260 may send an indication to the workout plan module 200 to redetermine the workout plan for the user given that the user performed the exercise or may send an indication that the user has requested a different exercise.

The user interface module 260 may receive requests for a recommended weight, number of sets, or number of repetitions from a user via the user interface. In particular, the user interface may display a plurality of exercises for the user to choose from, and upon receiving a selection, the user interface module 260 may send an indication of the exercise to the recommendation module 220. The user interface module 260 receives the recommendations from the recommendation module 220 and sends the recommendations for display via the user interface.

The user interface module 260 may also receive requests from a user for the user's capability for one or more exercises. The user interface module 260 may receive a request from the user interface for a current capability of the user for an exercise. The user interface module 260 sends the exercise to the capability module 240 to determine a capability of the user for the exercise. The capability of the user may be a weight for the exercise (e.g., the user can do one bench-press using 100 pounds) or a number of repetitions during a set (e.g., the user can do 32 pushups in one set). The user interface module 260 receives a capability of the user from the capability module 240 and displays the capability via the user interface.

Exercise Recommendation System Processes

Figure 3:
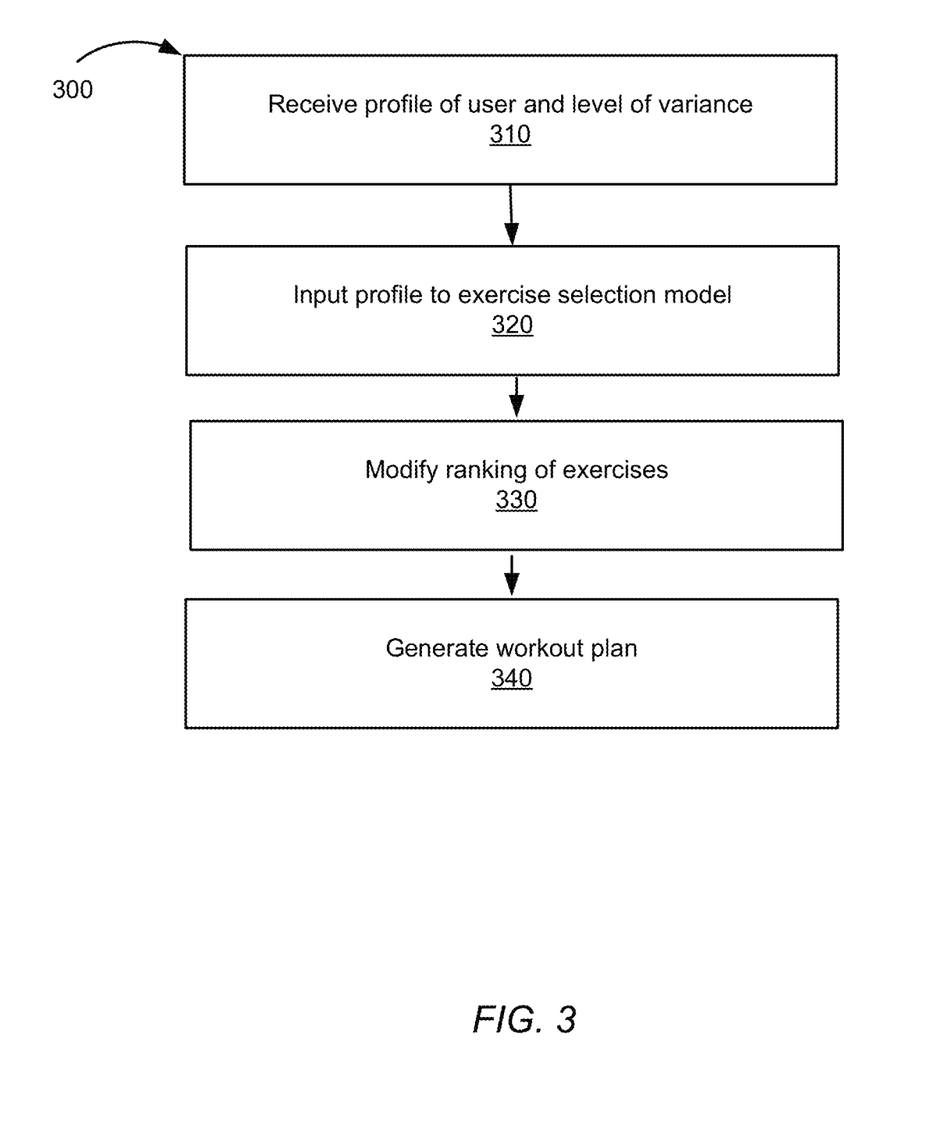
FIG. 3 is a flowchart illustrating a process for generating a workout plan, according to one embodiment.
Figure 4:
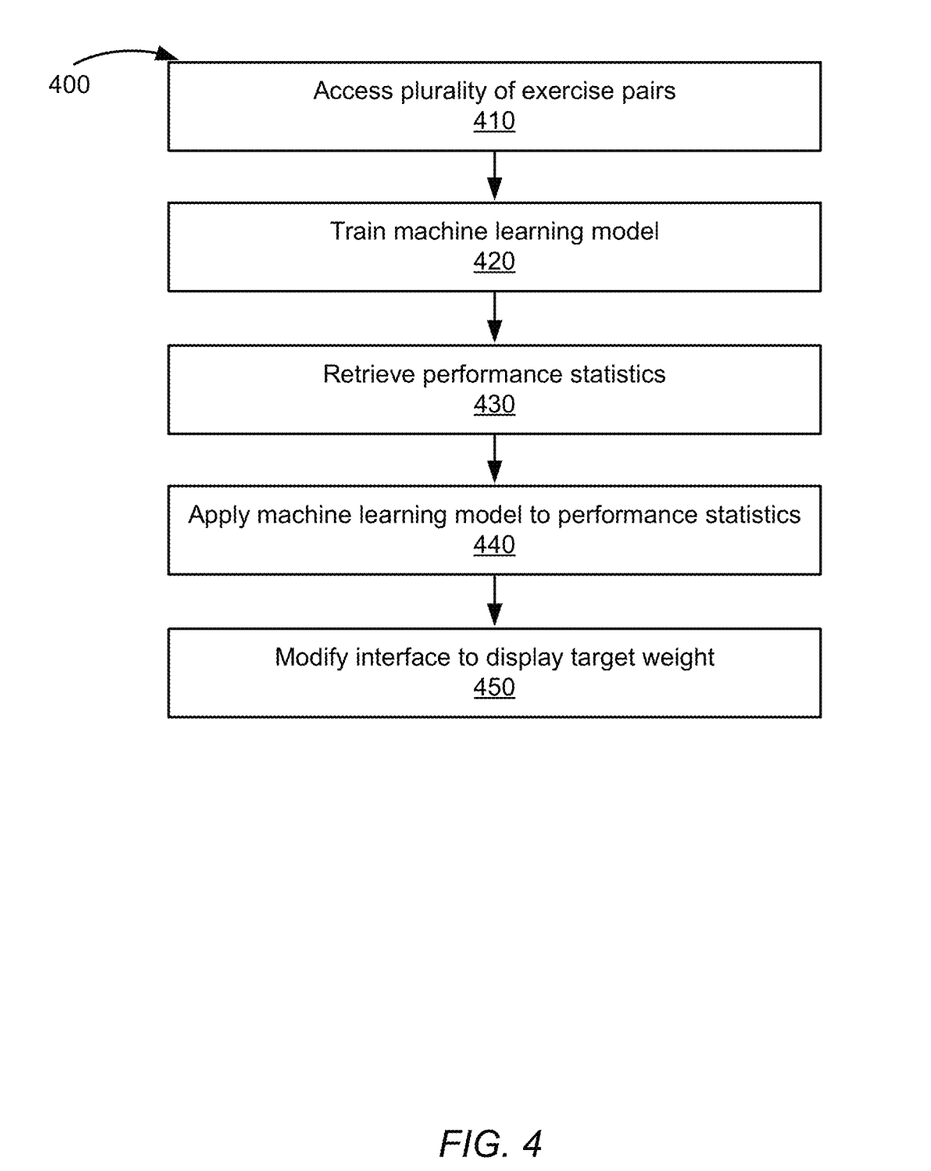
FIG. 4 is a flowchart illustrating a process for modifying an interface to display a target weight, according to one embodiment.
Figure 5:
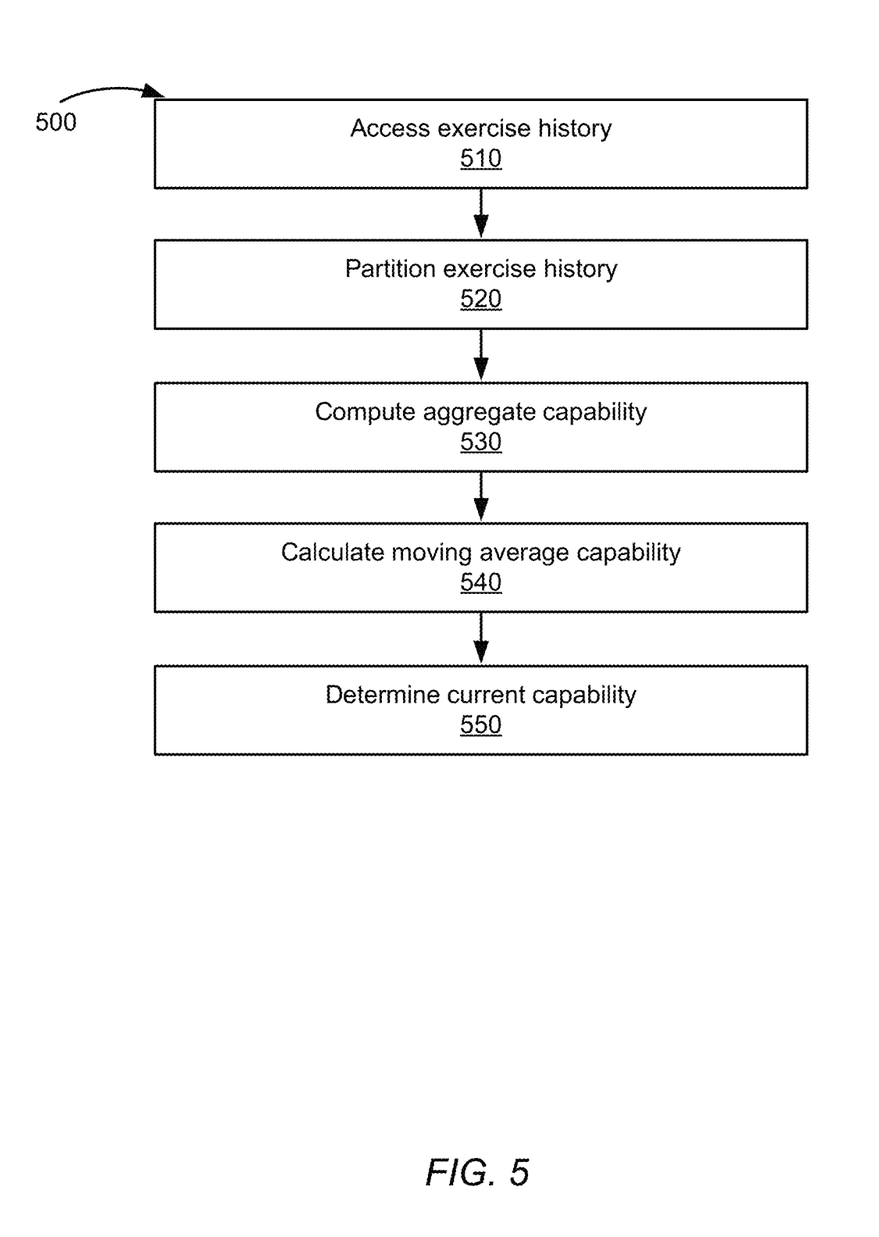
FIG. 5 is a flowchart illustrating a process for determining a current capability of a user, according to one embodiment.

FIGS. 3, 4, and 5 include flowchart illustrating processes (300, 400, and 500) performed by the exercise recommendation system 100. Though reference is made to engines, modules, and models of the exercise recommendation system 100 for these processes, the processes can be used by other online systems or mobile applications.

FIG. 3 illustrates a process 300 for generating a workout plan, according to one embodiment. The user interface module 250 receives 310 a profile of a user and a level of variance selected by the user via a user interface, both of which the user interface module 250 sends to the workout plan module 200 and/or stores in the user profile datastore 270. The workout plan module 200 inputs 320 the profile to the exercise selection model 210, and the exercise selection model 210 is configured to rank a set of exercises for a user to perform based on the user's profile. The set of exercises may be specific to the user or may be standard for the exercise recommendation system 100. The workout plan module 200 modifies 330 the ranking of exercises based on the profile and the level of variance. For instance, the workout plan module 200 may modify the ranking a greater amount for a first level of variance than for a second level of variance lower than the first level of variance. The workout plan module 200 generates 340 a workout plan for the user, where the workout plan comprises a threshold number of exercises selected based on the modified ranking.

It is appreciated that although FIG. 3 illustrates a number of interactions according to one embodiment, the precise interactions and/or order of interactions may vary in different embodiments. For example, in some embodiments, modifying the ranking comprises alerting scores of one or more exercise based on the user profile. In particular, the workout module 200 may reduce the scores of exercises that have low ratings from the user, that were recently performed by the user, that target muscle groups different from those specified in the user's exercise goals, that require equipment the user does not have, that conflict with physical ailments of the user, and the like. Further, the workout module 200 may increase the scores of exercises that target muscle groups specified by the user's exercise goals, that burn calories similar to a target set by the user, or the like. The workout module 200 may re-rank the exercises based on the altered scores and select exercises for the workout plan based on the new ranking.

FIG. 4 illustrates a process 400 for modifying a user interface to display a target weight. In particular, the recommendation module 220 accesses 410 a plurality of exercises pairs from the exercise datastore 280. Each exercise pair is labeled with performance statistics of users who have completed the exercises of the exercise pair. In some embodiments, each exercise pair may further be labeled based on muscle group capabilities, such as which muscle groups each exercise works. The training module 250 trains 420 a machine learning model (e.g., the weight recommendation model 230) using the plurality of exercise pairs. The machine learning model is configured to determine a weight to recommend to a user for a first exercise based on performance statistics associated with one or more second exercises, where each second exercise is within an exercise pair with the first exercise. In some embodiments, the machine learning model is further configured to determine a number of repetitions to recommend to the user for the first exercise based on the performance statistics of the user associated with the one or more second exercises.

The recommendation module 220 retrieves 430 performance statistics of a target user from the user profile datastore 270. The performance statistics may include a weight for each of one or more exercises previously performed by the target user, a weight of the user, a current muscle mass of the user, an average exercise time, a current capability of a user, and a number of repetitions for each of one or more exercises previously performed by the target user. The recommendation module 220 applies 440 the machine learning model to the performance statistics and a target exercise to determine a target weight to recommend to the target user for the target exercise. The recommendation module 220 modifies 450 the user interface displayed at a client device 120 of the target user to include the target weight determined by the machine learning model.

It is appreciated that although FIG. 4 illustrates a number of interactions according to one embodiment, the precise interactions and/or order of interactions may vary in different embodiments. For example, in some embodiments, responsive to receiving a request via the user interface for a target weight or target number of repetitions for an exercise, the recommendation module 220 applies the machine learning model to the performance statistics of the target user and the exercise to determine a target weight and/or target number of repetitions to recommend to the user for the exercise and modifies the user interface to include the target weight and/or target number of repetitions.

FIG. 5 illustrates a process 500 for determining a current capability of a user, according to one embodiment. The capability module 240 accesses 510 an exercise history for a user from the user profile datastore 270. The exercise history comprises one or more exercises performed by the user and a capability of the user each time the user performed the exercise. In some embodiments, the exercise history may further comprise information about exercises performed within a recent time period and, for each exercise in the exercise history, a number of sets performed by the user, a number of repetitions performed by the user for each set, and a weight used by the user.

The capability module 240 partitions 520 the exercise history into a plurality of time periods, and for each time period, the capability module 240 computes 530 an aggregate capability for each of the one or more exercises based on the capabilities of the user in performing each exercise during the time period. The capability module 240 calculates 540 a moving average capability of the user for each exercise based on the aggregate capabilities. In some embodiments, the capability module 240 may apply exponential smoothing to the moving average capability. The capability module 240 determines 550 the current capability of the user for each exercise based on the moving average capability, where the current capability of the user for each exercise is discounted at least in part based on how recently the user performed the exercise.

It is appreciated that although FIG. 5 illustrates a number of interactions according to one embodiment, the precise interactions and/or order of interactions may vary in different embodiments. For example, in some embodiments, responsive to determining that a threshold amount of time has passed since the user has exercised, the capability module 240 may decay the current capability of the user based on the threshold amount of time that has passed and use the decayed current capability as the current capability for the user. In other embodiments, the capability module 240 may modify a user interface of a client device 120 associated with the user to display the current capability responsive to receiving a request via the user interface for the current capability.

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for generating a workout plan, the method comprising:
receiving a user profile for a user, the user profile including a history of exercises the user has performed, available gym equipment, and one or more exercise goals;
receiving a selection indicating a level of variance for a workout plan, wherein the user selects the level of variance by adjusting an interactive element of a graphical user interface displayed on a mobile device operated by the user, the level of variance representing a preferred level of variety in workout plans in one or more of the following: exercises, workout length, and focused muscle group;
inputting, by a processor, the user profile to an exercise selection model to rank a set of exercises for a user to perform based on the history of exercises the user has performed, the available gym equipment, and the one or more exercise goals, wherein the exercise selection model is a machine learning model trained to rank the set of exercises based on a training dataset comprising exercise histories collected for a population of users labeled with available exercise equipment, exercise goals, and a corresponding user profile;
modifying, by the processor, the ranking of exercises based on the level of variance selected by the user, wherein the modification comprises:
selecting a random set of exercises performed by the user within a threshold period of time based on the level of variance; and
adjusting rankings of the selected random set of exercises;
selecting a subset of exercises to be included in a workout plan based on the modified ranking of exercises and the level of variance, wherein the subset of exercises includes a greater variety of exercises for a higher level of variance than a lower level of variance;
applying, by the processor, a weight recommendation machine learning model to performance statistics of the user and a first exercise from the subset of exercises, the weight recommendation machine learning model trained using supervised learning on training data including a plurality of exercise pairs each labeled with current capabilities of and weight recommendations for users that completed both exercises in a respective exercise pair, wherein training the weight recommendation machine learning model using supervised learning creates a function that maps the exercise pairs to the respective current capabilities and weight recommendations;
receiving, from the weight recommendation machine learning model, a current target weight to recommend to the user for the first exercise; and
modifying, by the processor in real-time, the graphical user interface to display the current target weight and the first exercise.

2. The method of claim 1, wherein the user profile includes a recency of each exercise in the history of exercises, exercise restrictions of the user, and one or more ratings for one or more exercises previously performed by the user.

3. The method of claim 1, wherein the level of variance indicates how much to vary one or more of each exercise, workout length, and focused muscle group in the workout plan for the user.

4. The method of claim 1, further comprising modifying the graphical user interface to display a workout plan that comprises a threshold number of top-ranked exercises in the modified ranking.

5. The method of claim 1, wherein modifying the ranking of exercises further comprises:
altering scores of one or more exercises recently performed by the user.

6. The method of claim 1, further comprising:
removing one or more exercises with low ratings by the user from the modified ranking.

7. The method of claim 1, further comprising:
removing one or more exercises associated with equipment the user does not have from the modified ranking.

8. A non-transitory computer-readable storage medium comprising instructions that when executed by a processor cause the processor to:
receive a user profile for a user, the user profile including a history of exercises the user has performed, available gym equipment, and one or more exercise goals;
receive a selection indicating a level of variance for a workout plan, wherein the user selects the level of variance by adjusting an interactive element of a graphical user interface displayed on a mobile device operated by the user, the level of variance representing a preferred level of variety in workout plans in one or more of the following: exercises, workout length, and focused muscle group;
input the user profile to an exercise selection model to rank a set of exercises for a user to perform based on the history of exercises the user has performed, the available gym equipment, and the one or more exercise goals, wherein the exercise selection model is a machine learning model trained to rank the set of exercises based on a training dataset comprising exercise histories collected for a population of users labeled with available exercise equipment, exercise goals, and a corresponding user profile;
modify the ranking of exercises based on the level of variance selected by the user, wherein the modification comprises instructions that cause the processor to:
select a random set of exercises performed by the user within a threshold period of time based on the level of variance; and
adjust rankings of the selected random set of exercises;
select a subset of exercises to be included in a workout plan based on the modified ranking of exercises and the level of variance, wherein the subset of exercises includes a greater variety of exercises for a higher level of variance than a lower level of variance;
applying, by the processor, a weight recommendation machine learning model to performance statistics of the user and a first exercise from the subset of exercises, the weight recommendation machine learning model trained using supervised learning on training data including a plurality of exercise pairs each labeled with current capabilities of and weight recommendations for users that completed both exercises in a respective exercise pair, wherein training the weight recommendation machine learning model using supervised learning creates a function that maps the exercise pairs to the respective current capabilities and weight recommendations;
receiving, from the weight recommendation machine learning model, a current target weight to recommend to the user for the first exercise; and
modifying, by the processor in real-time, the graphical user interface to display the current target weight and the first exercise.

9. The non-transitory computer-readable storage medium of claim 8, wherein the user profile includes a recency of each exercise in the history of exercises, exercise restrictions of the user, and one or more ratings for one or more exercises previously performed by the user.

10. The non-transitory computer-readable storage medium of claim 8, wherein the level of variance indicates how much to vary one or more of each exercise, workout length, and focused muscle group in the workout plan for the user.

11. The non-transitory computer-readable storage medium of claim 8, the instructions further comprising modifying the graphical user interface to display a workout plan that comprises a threshold number of top-ranked exercises in the modified ranking.

12. The non-transitory computer-readable storage medium of claim 8, wherein instructions for modifying the ranking of exercises further comprise instructions that cause the processor to alter scores of one or more exercises recently performed by the user.

13. The non-transitory computer-readable storage medium of claim 8, further comprising instructions that cause the processor to remove one or more exercises with low ratings by the user from the modified ranking.

14. The non-transitory computer-readable storage medium of claim 8, further comprising instructions that cause the processor to remove one or more exercises associated with equipment the user does not have from the modified ranking.

15. A computer system comprising:
a computer processor; and
a non-transitory computer-readable storage medium storage instructions that when executed by the computer processor perform actions comprising:
receive a user profile for a user, the user profile including a history of exercises the user has performed, available gym equipment, and one or more exercise goals;
receive a selection indicating a level of variance for a workout plan, wherein the user selects the level of variance by adjusting an interactive element of a graphical user interface displayed on a device operated by the user, the level of variance represents a preference for variety in workout plans in one or more of the following: exercises, workout length, and focused muscle group;
input, by the computer processor, the user profile to an exercise selection model to rank a set of exercises for a user to perform based on the history of exercises the user has performed, the available gym equipment, and the one or more exercise goals, wherein the exercise selection model is a machine learning model trained to rank the set of exercises based on a training dataset comprising exercise histories collected for a population of users labeled with available exercise equipment, exercise goals, and a corresponding user profile;
modify the ranking of exercises based on the level of variance selected by the user, wherein the modification comprises instructions that cause the computer processor to:
select a random set of exercises performed by the user within a threshold period of time based on the level of variance; and
adjust rankings of the selected random set of exercises;
select a subset of exercises to be included in a workout plan based on the modified ranking of exercises and the level of variance, wherein the subset of exercises includes a greater variety of exercises for a higher level of variance than a lower level of variance;
apply, by the computer processor, a weight recommendation machine learning model to performance statistics of the user and a first exercise from the subset of exercises, the weight recommendation machine learning model trained using supervised learning on training data including a plurality of exercise pairs each labeled with current capabilities of and weight recommendations for users that completed both exercises in a respective exercise pair, wherein training the weight recommendation machine learning model using supervised learning creates a function that maps the exercise pairs to the respective current capabilities and weight recommendations;

receive, from the weight recommendation machine learning model, a current target weight to recommend to the user for the first exercise; and modify, by the computer processor in real-time, the graphical user interface to display the current target weight and the first exercise.

16. The computer system of claim 15, wherein the user profile includes a recency of each exercise in the history of exercises, exercise restrictions of the user, and one or more ratings for one or more exercises previously performed by the user.

17. The computer system of claim 15, wherein the level of variance indicates how much to vary one or more of each exercise, workout length, and focused muscle group in the workout plan for the user.

18. The computer system of claim 15, the instructions further comprising modifying the graphical user interface to display a workout plan comprises a threshold number of top-ranked exercises in the modified ranking.

19. The computer system of claim 15, wherein instructions for modifying the ranking of exercises further comprise instructions that cause the computer processor to alter scores of one or more exercises recently performed by the user.

20. The computer system of claim 15, further comprising instructions that cause the processor to remove one or more exercises with low ratings by the user from the modified ranking.

* * * * *